(12) United States Patent
Ponder

(10) Patent No.: US 9,936,974 B2
(45) Date of Patent: Apr. 10, 2018

(54) LAPAROSCOPIC UTERINE MANIPULATOR ASSEMBLY AND METHODOLOGY FOR USE

(75) Inventor: Jerome V. Ponder, Fayetteville, NC (US)

(73) Assignee: Jerome V. Ponder, Fayetteville, NC (US)

( * ) Notice: Subject to any disclaimer, the term of this patent is extended or adjusted under 35 U.S.C. 154(b) by 918 days.

(21) Appl. No.: 13/539,620

(22) Filed: Jul. 2, 2012

(65) Prior Publication Data

US 2013/0018386 A1 Jan. 17, 2013

Related U.S. Application Data

(60) Provisional application No. 61/506,827, filed on Jul. 12, 2011.

(51) Int. Cl.
*A61B 17/42* (2006.01)
*A61B 17/00* (2006.01)
*A61B 17/22* (2006.01)

(52) U.S. Cl.
CPC .......... *A61B 17/4241* (2013.01); *A61B 2017/00477* (2013.01); *A61B 2017/22069* (2013.01)

(58) Field of Classification Search
CPC ................................. A61L 317/4241
USPC ............... 606/119, 190, 191, 205, 211, 139; 600/591, 204; 604/279
See application file for complete search history.

(56) References Cited

U.S. PATENT DOCUMENTS

| | | | |
|---|---|---|---|
| 7,121,997 B2 * | 10/2006 | Kammerer et al. | 600/30 |
| 2008/0119868 A1 * | 5/2008 | Sharp et al. | 606/119 |
| 2010/0280524 A1 * | 11/2010 | Lopez Zepeda | 606/119 |

* cited by examiner

*Primary Examiner* — Anh Dang

(57) ABSTRACT

Exemplary embodiments of the present invention comprise a laparoscopic uterine manipulator device assembly. The laparoscopic uterine manipulator assembly comprises a laparoscopic control device configured for insertion into the abdomen-pelvic cavity of a patient. The laparoscopic uterine manipulator assembly further comprises a uterine manipulator device, the uterine manipulator device configured for insertion and advancement through a vaginal and uterine cavity. A primary member of a device coupling mechanism of the uterine manipulator device is mechanically engaged with a secondary member of the device coupling mechanism of the laparoscopic control device, resulting in the construction of an assembly comprising the laparoscopic control device and the uterine manipulator device. Assembled, the laparoscopic uterine manipulator assembly allows an individual user to utilize the device to engage and reposition the patient's uterus in a manner that allows for the performance of a gynecological laparoscopic medical procedure for the maximum benefit of the patient.

9 Claims, 3 Drawing Sheets

LAPAROSCOPIC UTERINE MANIPULATOR ASSEMBLY AND METHODOLOGY FOR USE

RELATED APPLICATION

This application claims priority to U.S. Provisional Patent Application No. 61/506,827 filed Jul. 12, 2011 entitled "UTERINE CHANDELIER DEVICE AND METHODOLOGY FOR USAGE", the entirety of which herein is hereby incorporated by reference.

BACKGROUND OF THE INVENTION

Field of the Invention

This invention relates to medical devices, more specifically the invention relates to medical devices utilized within the performance of gynecological surgeries.

Description of the Background

Gynecological laparoscopic surgeries have become increasingly accepted due to the realized advantages of performing less invasive medical procedures. However, within many procedures the concurrent usage of multiple surgical instruments is required. As such, it is necessitated that the operators of said surgical instruments work cautiously and meticulously in concert to competently perform said gynecological procedures.

Therefore, it would be advantageous to provide a device and a methodology for the performance of gynecological laparoscopic procedures wherein a single individual can be charged with operating and manipulating the most vital surgical instruments during a procedure.

SUMMARY OF THE INVENTION

The shortcomings of any prior art are overcome and additional advantages are provided through the provision of a uterine manipulator 100, wherein the uterine manipulator 100 is configured for insertion into and advancement through the vaginal and uterine cavity of a patient, being ultimately moved towards the distal wall of the patient's uterus. Exemplary embodiments of the uterine manipulator 100 comprise a shaft body 102 of a predetermined length and a uterine placement handle 104. The uterine placement handle 104 being comprised at a proximate end of the uterine manipulator 100 and being disposed towards the individual that is inserting the uterine manipulator 100 into the patient.

The uterine manipulator 100 further comprises at least two cavity sealing devices 108. Each cavity sealing device 108 is physically engaged with the shaft body 102, wherein the cavity sealing devices 108 are configured to surround the shaft body 102 at predetermined segments along the length of the shaft body 102. The uterine manipulator 100 additionally comprises a primary member 112 of a device coupling mechanism 204 comprised at the distal end of the shaft body 102.

Further exemplary embodiments of the present invention comprise a laparoscopic uterine manipulator assembly 200. The laparoscopic uterine manipulator assembly 200 comprises a laparoscopic control device 202 that is configured for insertion into the abdomen-pelvic cavity of a patient. As constructed, the laparoscopic control device 202 has a proximate end situated towards the device 202 operator and a distal end that is disposed away from the operator. The distal end of the laparoscopic control device 202 further comprising a secondary member 206 of a device coupling mechanism 204.

The laparoscopic uterine manipulator assembly 200 also comprises a uterine manipulator 100, the uterine manipulator 100 being configured for insertion and advancement through a vaginal and uterine cavity towards a distal uterine wall. The uterine manipulator 100 is comprised of a shaft body 102 of predetermined length and having a proximate end, a distal end, and a uterine placement handle 104 that is comprised at the proximate end of the shaft body 102.

The uterine manipulator 100 yet further comprises a tissue-penetrating component 110 that is situated at the distal end of the shaft body 102; the tissue-penetrating component 110 is configured to perforate the distal uterine wall, thus forming an opening in the uterine wall. The primary member 112 of the device coupling mechanism 204 is located at the distal end of the shaft body 102. The primary member 112 of the device coupling mechanism 204 is configured to be advanced through a perforated opening in the uterine wall and thereafter be mechanically engaged with the secondary member 206 of the device coupling mechanism 204 of the laparoscopic control device 202, the result being the construction of an assembly 200 comprised of the laparoscopic control device 202 and the uterine manipulator 100. As assembled, the laparoscopic uterine manipulator assembly 200 allows an individual user to utilize the device 200 to engage and reposition a patient's uterus during a surgical procedure.

An additional exemplary embodiment of the present invention comprises a methodology for the utilization of a laparoscopic uterine manipulator assembly 200 for the conduction of a hysterectomy medical procedure on a medical patient. The method comprises advancing a uterine manipulator 100 through the vaginal cavity, cervix, and uterine cavity of a patient towards a distal uterine wall of the patient's uterus. As configured, the uterine manipulator 100 comprises a tissue-penetrating component 110 situated at the distal end of the uterine manipulator 100 and a primary member 112 of a device coupling mechanism 204 located at the distal end of the uterine manipulator 100.

The tissue-penetrating component 110 of the uterine manipulator 100 is utilized to perforate the uterus wall, wherein thereafter the primary member 112 of the device coupling mechanism 204 of the uterine manipulator 100 is advanced through the perforated opening of the uterine wall. As part of the same procedure, the laparoscopic control device 202 is advanced into the abdomen-pelvic cavity of the patient towards the perforated uterine wall, the laparoscopic control device 202 comprising a proximate end and a distal end. The distal end of the laparoscopic control device 202 comprising a secondary member 206 of the device coupling mechanism 204.

Once positioned within the abdomen-pelvic cavity of the patient the secondary member 206 of the device coupling mechanism 204 of the laparoscopic control device 202 is mechanically engaged with the primary member 112 of the device coupling mechanism 204 of the uterine manipulator 100, resulting in the construction of an assembly 200 comprised of the laparoscopic control device 202 and the uterine manipulator 100.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

Figure 1:
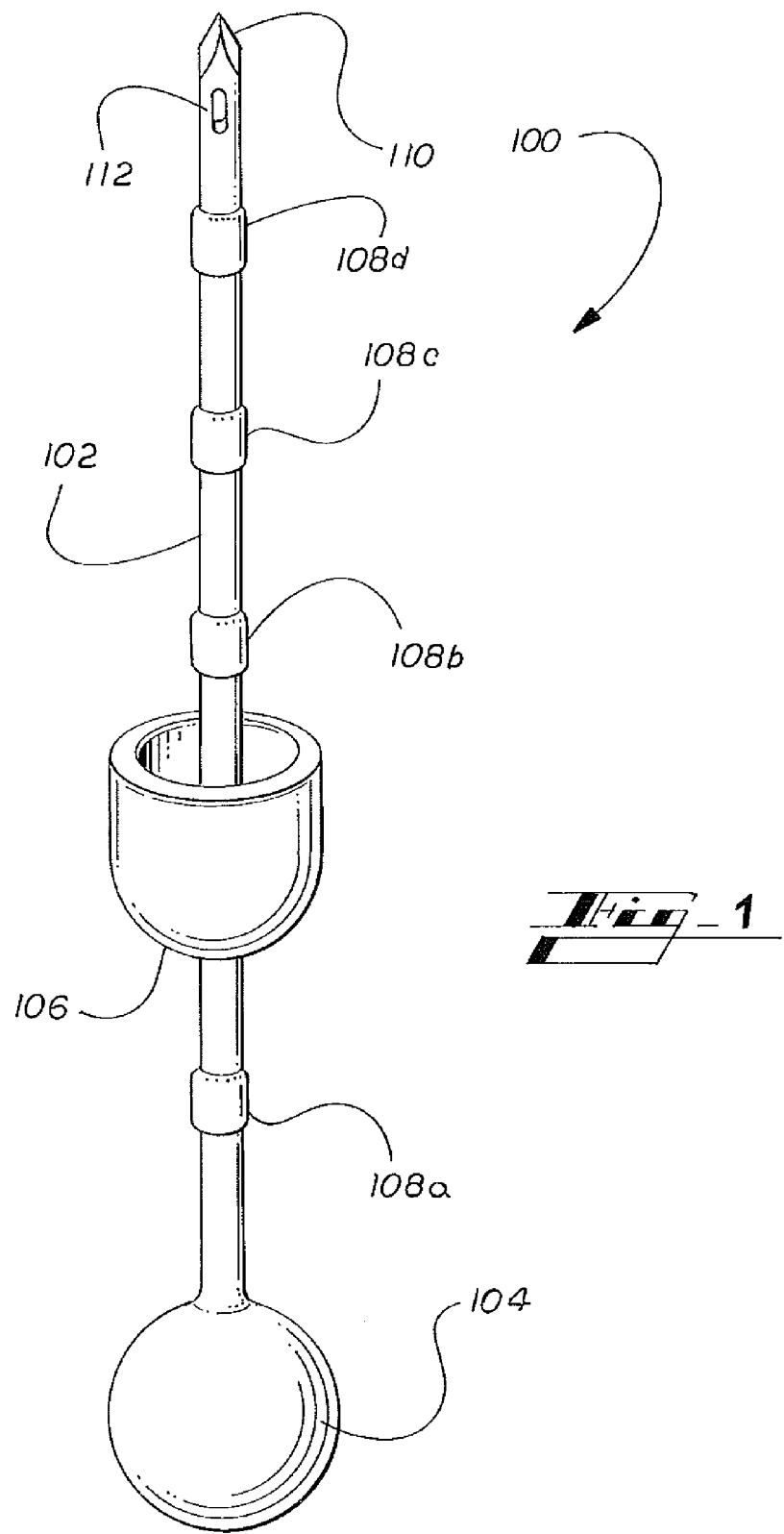
FIG. 1 illustrates an exemplary embodiment of a uterine manipulator in accordance with aspects of the present invention.

The detailed description explains the exemplary embodiments of the invention, together with advantages and features, by way of example with reference to the drawings.

DETAILED DESCRIPTION OF THE INVENTION

One or more exemplary embodiments of the invention are described below in detail. The disclosed embodiments are intended to be illustrative only since numerous modifications and variations therein will be apparent to those of ordinary skill in the art. In reference to the drawings, like numbers will indicate like parts continuously throughout the views. Herein, the use of the terms primary, secondary, etc., do not denote any order or importance, but rather the terms primary, secondary, etc., are used to distinguish one element from another. Furthermore, the use of the terms a, an, etc., do not denote a limitation of quantity, but rather denote the presence of at least one of a referenced item.

Current laparoscopic hysterectomy procedures usually are affairs necessitating the need of a collective team of skilled individuals to perform delicate medical procedures. At a minimum, a surgical team can consist of a lead Gynecologist (GYN) and a surgical technical assistant. Within a typical gynecological laparoscopic surgical procedure the GYN is charged with the control and operation of any laparoscopic surgical devices, while the surgical technician is charged with the insertion and advancement of a uterine manipulator into the vaginal and uterine cavities of a patient. The surgical technician also has the additional duties of manipulating the uterus by use of the device placed within the uterus in accordance with verbal instructions provided by the GYN to assist the GYN in ensuring that the uterus is in proper placement for the resulting surgical removal of the organ.

As with any surgical procedure, the proper control and manipulation of all surgical instruments is necessitated to assure for the safety of the patient and the success of the operation. In some instances the delegation of specific surgical responsibilities to individuals other than the performing surgeon would not be to the utmost benefit for the patient's behalf—and thus not ensure that the patient receive the highest amount of technical surgical performance care.

Therefore, exemplary embodiments of the present invention seek to remedy the above-mentioned inadequacies of current surgical procedures by assuring that the performing GYN from the onset of a gynecological hysterectomy procedure have an enhanced amount of control over the necessitated surgical instruments, the operation of said surgical instruments, and having the capability to be able to positional manipulate the uterus in a manner that allows for the performance of a surgical procedure for the maximum benefit of a patient.

Exemplary embodiments of the present invention comprise a laparoscopic uterine manipulator assembly. The laparoscopic uterine manipulator assembly is comprised of two component surgical instruments, those being a uterine manipulator and a laparoscopic control device, wherein both devices are supplied with mechanical connector components. The mechanical connector components of the device elements are mechanically engaged to form a singular laparoscopically controlled assembly of the component devices. Thereafter, the fully formed assembly has the capability to allow a surgeon within a surgical procedure to laparoscopically manipulate the position of a patient's uterus in a manner that will ensure that the uterus be removed in a most safe and efficient manner.

Figure 2:
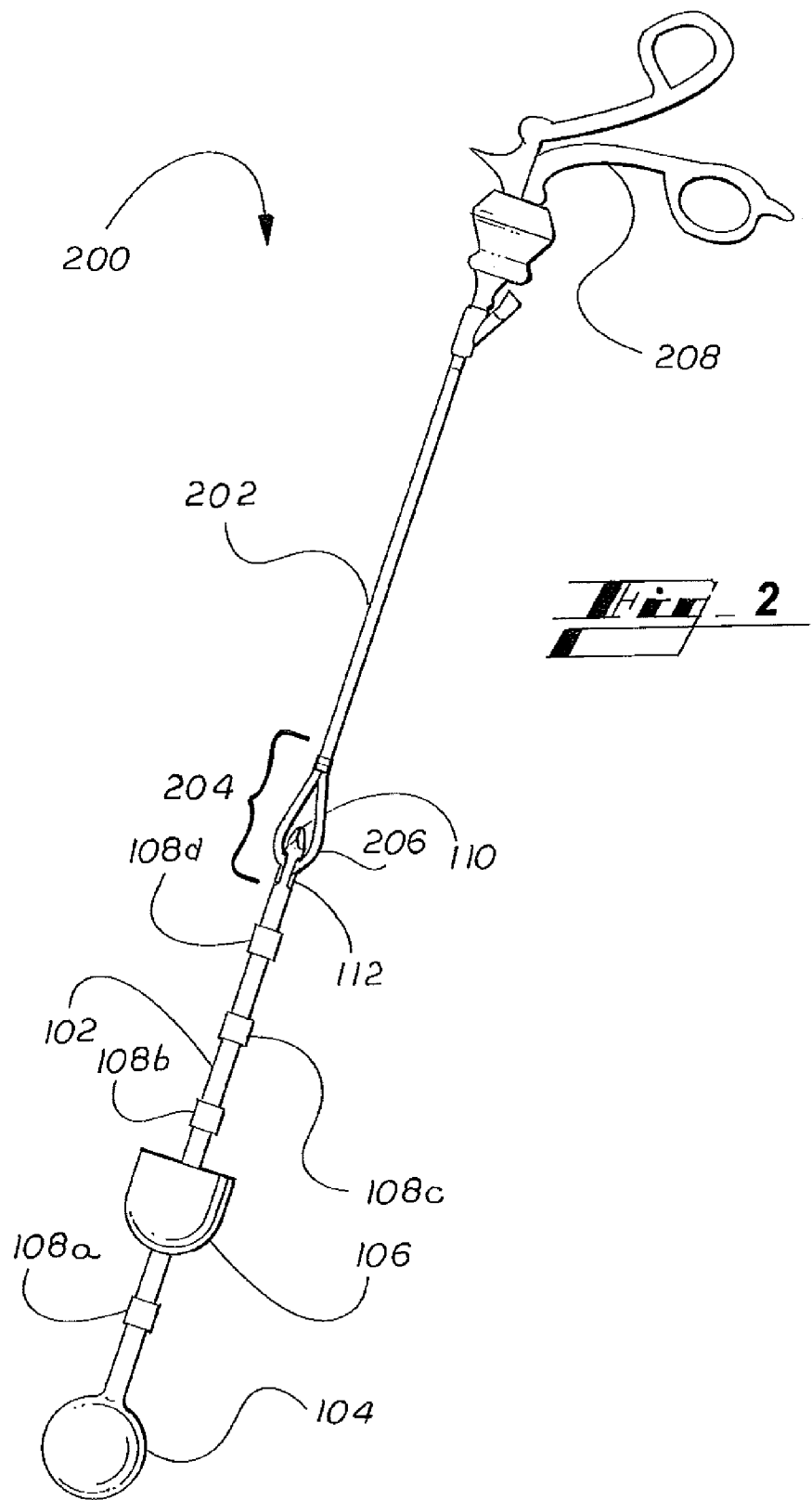
FIG. 2 illustrates an exemplary embodiment of a laparoscopic uterine manipulator assembly in accordance with aspects of the present invention.

In function, the laparoscopic uterine manipulator assembly is assembled and utilized inside of the patient during a surgical procedure as needed by a surgeon. Referring to FIGS. 1 and 2, shown is an illustration of a uterine manipulator 100 that may be implemented within exemplary embodiments of the laparoscopic uterine manipulator device assembly 200 as presently described. The uterine manipulator 100 is specifically designed to be inserted into the vaginal cavity of a patient, thereafter the device 100 is advanced through the vaginal cavity and moved towards the uterus of the patient, wherein the leading edge of the uterine manipulator 100 is advanced past the cervix into the uterine cavity before coming to rest at the distal wall of the uterus.

As shown, the uterine manipulator 100 comprises a shaft body 102. The shaft body 102 further comprises at a proximate end that is situated towards the device 100 insertion operator a placement handle 104. Situated away from the device 100 operator at a distal end of the shaft body 102 is a primary device coupling mechanism member 112 and a tissue penetrating component 110. The tissue penetrating component 110 serves as an edged uterine perforation device during surgical procedures. As the uterine manipulator 100 is advanced through the vaginal and uterine cavities, the tissue penetrating component will come to rest at the far wall of the patient's uterus. The surgeon will then apply an appropriate amount of force to the uterine manipulator 100 to engage the uterine wall and use the tissue penetrating component 110 to perforate the uterine wall, allowing for the tissue penetrating component 110 and the primary device coupling mechanism member 112 to be advanced through the perforation in the uterine wall.

To stop the forward motion of the uterine manipulator 100 through the uterine wall a cervical anchoring device 106 is provided with the uterine manipulator 100. In function, the cervical anchoring device 106 is configured to physically engage the cervix at the junction of the vagina and cervix and slightly lift the uterus from its resting position at the vagina, thus allowing for the position of the uterus to be shifted according to the needs of the operating physician. As shown, the cervical anchoring device 106 comprises a cervical cup, wherein the shaft 102 of the uterine manipulator device 100 is inserted or positioned via the center of the cervical cup. The cervical cup is fixed in position at a predetermined area along the length of the uterine manipulator 100. Upon the cervical anchoring device 106 engaging the cervix, the forward motion of a uterine manipulator 100 progressing through the vaginal and uterine cavities is effectively stopped.

Once the uterine manipulator 100 has been inserted into the vaginal and uterine cavities and the tissue penetrating component 110 and the primary device coupling mechanism member have cleared the perforation within the uterine wall, the device 100 needs to be stabilized within the vaginal and uterine cavities. As shown, cavity sealing devices 108 a-d are provided to assist in the stabilization of the uterine manipulator device 100 during the surgical procedure. Each cavity sealing device 108 is physically engaged with the shaft body 102 to provide a physical means to secure the uterine manipulator device 100 in place within the patient. As shown, the cavity sealing devices 108 a-d are configured to surround the shaft body 102 at predetermined segments along the length of the shaft body 102. Within exemplary embodiments of the present invention the cavity sealing devices 108 comprise balloons. Within the exemplary embodiments of the present invention the cavity sealing balloons 108 are constructed of a pliable medical grade material (e.g., silicon, plastic, etc.) and have the capability to be inflated and deflated to predetermined volumes, depending on the discretion of the performing surgeon.

The shaft body 102 of the uterine manipulator 100 can be manufactured according to varying predetermined length specifications. By furnishing shafts 102 of varying lengths procedural surgeons are provided with the ability to compensate for the contrasting degrees of physiological differences that can occur between patients. The uterine manipulator 100 and all of its elements can be constructed from pliable medical grade materials (e.g., silicon, plastic, etc.) or metals. In particular, the shaft body 102 of the uterine manipulator 100 is configured to be of a flexible design to assist in the ease of inserting the device 100 into the vaginal and uterine cavities of the patient. The cervical cup of the cervical anchoring device 106 can further be provided in varying sizes to assist the surgeon in compensating for a patient's physiological differences.

As shown in FIG. 2 the uterine manipulator 100 and the laparoscopic control device 202 are collectively referred to as the laparoscopic uterine manipulator assembly 200. The laparoscopic control device 202 comprises at a proximate end situated at a position relative to the device operator a device control handle 208. Additionally, at a distal end of the laparoscopic control device 202 is a secondary device coupling mechanism member 206 of the device coupling mechanism 204. The primary 112 and secondary 206 device coupling mechanism members of the uterine manipulator 100 and the laparoscopic control device 202 being configured to be mechanically engaged in such a manner that the uterine manipulator 100 can be placed under the control of the laparoscopic control device 202. This configuration thus provides an individual laparoscopic uterine manipulator assembly 200 operator the ability to utilize the compound device 200 for the engagement and repositioning of the patient's uterus prior to the introduction of a laparoscopic tissue cutting instrument that will be used to surgically remove the patient's uterus.

As shown in FIG. 2, the primary and secondary members (112, 206) of the device coupling mechanism 204 respectfully comprise a retraction eyelet that is comprised at the distal end of the uterine manipulator 100 and a forceps grasping mechanism that is comprised at the distal end of the laparoscopic control device 202. As illustrated, the forceps grasping mechanism of the secondary device coupling member 206 comprises grasping surfaces, the grasping surfaces being designed to come into contact with one another when in a closed position. The forceps grasping mechanism is mechanically configured to be opened and closed by use of the laparoscopic control device 202 control handle 208. As designed, the forceps grasping surfaces meet together in a locked position in the space defined within the retraction eyelet of the primary device coupling member 112 when the forceps grasping mechanism is closed. Upon the engagement of the forceps grasping surfaces of the laparoscopic control device 202 within the retraction eyelet of the uterine manipulator 100, the uterine manipulator 100 is thereafter joined with and under the control of the laparoscopic control device 202.

Figure 3:
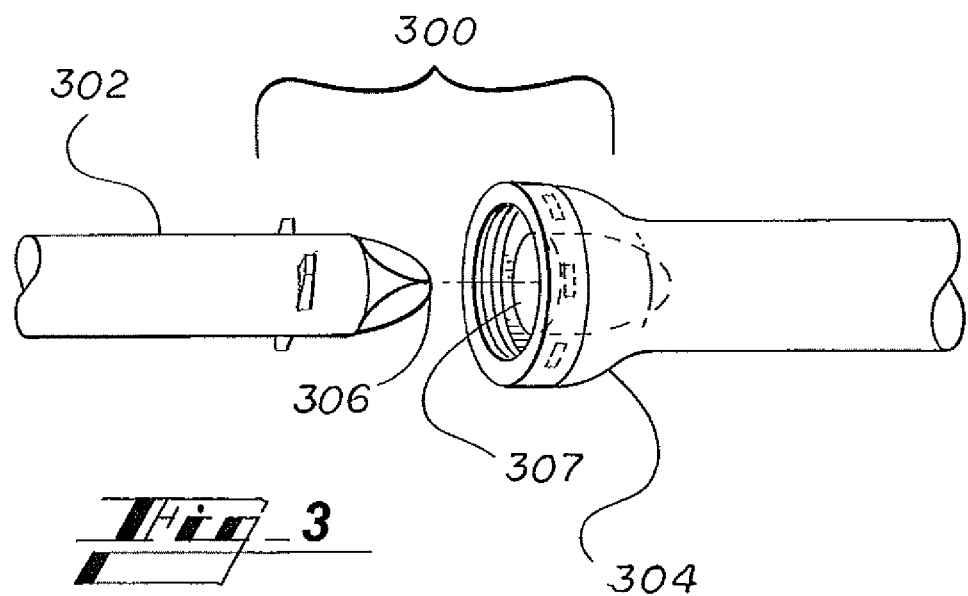
FIG. 3 illustrates an exemplary embodiment of primary and secondary members of a device coupling mechanism in accordance with aspects of the present invention.
Figure 4:
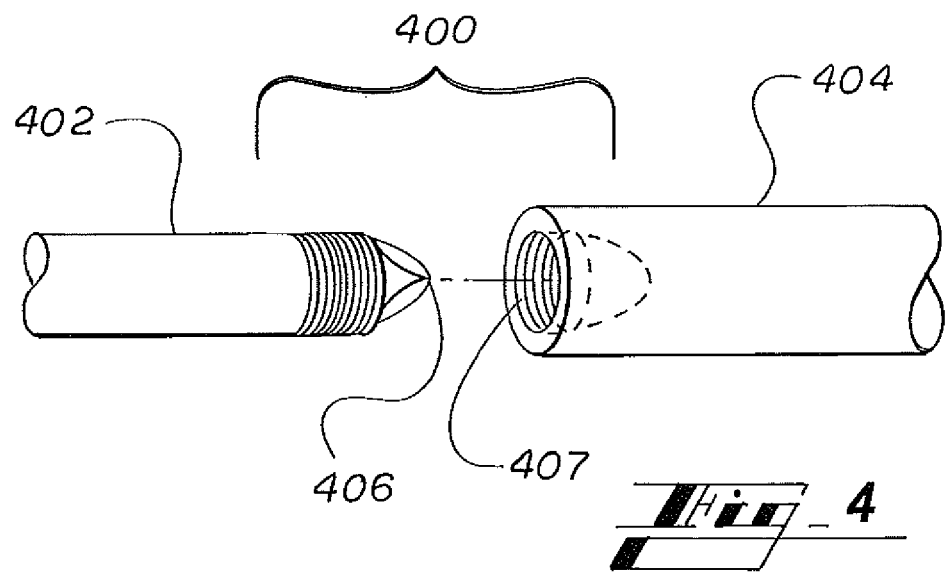
FIG. 4 illustrates an exemplary embodiment of primary and secondary members of a device coupling mechanism in accordance with aspects of the present invention.

Within further exemplary embodiments of the present invention the laparoscopic control device 202 can comprise a fixed position control handle set 208. In this instance the device coupling mechanism 204 of the compound devices 100 and 202 can comprise a variety of functionally equivalent mechanical coupling mechanisms. For example, as shown in FIGS. 3 and 4, the primary and secondary members (302, 402, 304, and 404) of the device coupling mechanism 204 can comprise, but are not limited to, a bayonet member coupling apparatus 300 or a threaded member coupling apparatus 400. In the event that the laparoscopic control device 202 is provided with a fixed position control handle set 208 the alternative primary (302, 402) and secondary device coupling members (304, 404) can be provided as interchangeable coupling elements of the laparoscopic uterine manipulator assembly 200. This exemplary functional aspect thus provides for the swapping-out of coupling members of the laparoscopic uterine manipulator assembly 200 as need would dictate based upon the type of mechanical coupling connection between the devices (100, 202) determined to be necessitated by the operating procedure.

It can be seen that no matter the type of coupling design that is utilized the tissue penetrating component (306, 406) is ever present at the distal end of the uterine manipulator 100. As shown, the tissue penetrating components (306, 406) of these further exemplary embodiments are configured to rest in a recessed area (307, 407) provided within the secondary device coupling mechanism members (304, 404) once the primary and secondary coupling members (302, 402, 304, and 404) are mechanically engaged. Within the exemplary aspects of the present invention the tissue penetrating components (110, 306, and 406) can embody differing structural tissue penetrating configurations. Tissue penetrating component configurations can comprise, but are not limited to, a fixed-blade component, a multiple-edge component with a sharp end (as shown), a blunt tip component, and a dilating-tip component.

A further exemplary embodiment of the present invention relates to a methodology for the use of the laparoscopic uterine manipulator assembly 200 within a surgical operation for the removal of a uterus. Exemplary methodologies utilizing the laparoscopic uterine manipulator assembly 200 of the present invention are optimized to allow for the presiding surgeon to individually perform the assembly and utilization of the device for the engagement and repositioning of a patient's uterus during a gynecological hysterectomy procedure.

Within the surgical procedure at least three trocars are inserted into the abdomen-pelvic cavity of a patient through incisions that have been made in the patient's abdomen. These trocars are utilized for the introduction of ports into the abdomen-pelvic cavity of the patient wherein a laparoscopic camera, a tissue-cutting instrument, and a laparoscopic control device 202 are placed. The distal end of the uterine manipulator 100 is placed into the vaginal cavity by usage of the placement handle 104. Thereafter the uterine manipulator 100 is guided through the vaginal cavity, the cervix, and the uterine cavity towards the distal wall of the patient's uterus.

Once the tissue penetrating component 110 of the uterine manipulator 100 comes into contact with the uterine wall the performing surgeon, by manipulation of the placement handle 104, will place an appropriate amount of forward pressure upon the placement handle 104 and thus cause the tissue penetrating component 110 to perforate the uterus wall. Upon puncturing the uterus wall the physician further advances the tissue penetrating component 110 and the primary device coupling mechanism member 112 through the uterine wall and into the abdomen-pelvic cavity of the patient. Once this action has been completed the uterine manipulator 100 can be physically stabilized within the vaginal and uterine cavities at a predetermined position by inflating the cavity sealing devices 108 *a-d*; the cavity sealing devices 108 *a-d* being configured to provide a physical means of securing the uterine manipulator 100 in a static position within the patient.

The distal end of the laparoscopic control device 202 is advanced into the abdomen-pelvic cavity of the patient and moved towards the perforated uterine wall from where the distal end of the uterine manipulator 100 extends. Once in place within the abdomen-pelvic cavity near the uterus, the secondary member 206 of the device coupling mechanism 204 of the laparoscopic control device 202 is mechanically engaged with the primary member 112 of the device coupling mechanism 204 of the uterine manipulator 100 resulting in the construction of an assembly 200 that comprises the laparoscopic control device 202 and the uterine manipulator 100.

The resulting laparoscopic uterine manipulator assembly 200 is configured to allow the individual user controlling the laparoscopic handle 208 the capability to utilize the device 200 to engage and reposition the uterus of the patient. Upon completing the assembly of the laparoscopic uterine manipulator assembly 200, the performing surgeon will utilize the assembly 200 to place the uterus in the best position from where the surgeon can utilize a laparoscopic cutting instrument to separate at least the uterus from the body of the patient. Thereafter, the performing physician will disassemble the laparoscopic uterine assembly 200 by mechanically disengaging the laparoscopic control device 202 from the uterine manipulator 100. Lastly, the uterine manipulator 100 and the laparoscopic control device 202 are respectfully withdrawn from the vaginal and abdomen-pelvic cavities and the severed uterus is removed from the abdomen-pelvic cavity of the patient.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the claims.

What is claimed:

1. A laparoscopic uterine manipulator assembly, the laparoscopic uterine manipulator assembly comprising:
   a laparoscopic control device configured for insertion into the abdomen-pelvic cavity of a patient, the laparoscopic control device having a proximate end and a distal end, wherein the proximate end of the laparoscopic control device comprises a device control handle and the distal end of the laparoscopic control device comprises a secondary member of a device coupling mechanism; and
   a uterine manipulator device, the uterine manipulator device being configured for insertion and advancement through a vaginal and uterine cavity towards a distal uterine wall, the uterine manipulator device comprising:
      a shaft body, the shaft body comprising a predetermined length and having a proximate end and a distal end;
      a uterine placement handle, the uterine placement handle being comprised at the proximate end of the shaft body;
      a tissue-penetrating component situated at the distal end of the shaft body, the tissue-penetrating component being configured to perforate the distal uterine wall, thus forming an opening in the uterine wall; and
      a primary member of the device coupling mechanism comprised at the distal end of the shaft body, the primary member of the device coupling mechanism being configured to be advanced through a perforated opening in the uterine wall and thereafter be mechanically engaged with the secondary member of the device coupling mechanism of the laparoscopic control device, resulting in the construction of an assembly comprised of the laparoscopic control device and the uterine manipulator device, wherein the primary and secondary members of the device coupling mechanism comprise a latch-hook clasp closure apparatus, a bayonet closure apparatus, or a threaded closure apparatus;
   the laparoscopic uterine manipulator device assembly being configured to allow an individual user to utilize the assembly device under the control of the device control handle of the laparoscopic control device to engage and reposition the patient's uterus.

2. The assembly device of claim 1, wherein the uterine manipulator device further comprises at least two cavity sealing devices, each cavity sealing device being physically engaged to the shaft body, the at least two cavity sealing devices being configured to surround the shaft body at predetermined segments along the length of the shaft body.

3. The assembly device of claim 2, wherein the uterine manipulator further comprises a cervical anchoring device, the cervical anchoring device configured to engage the cervix at a junction of the vagina and cervix.

4. A method for the utilization of a laparoscopic uterine manipulator assembly for the performance of a hysterectomy, the methodology comprising:
   advancing a distal end of a uterine manipulator device through the vaginal cavity and uterine cavity towards a distal uterine wall, the uterine manipulator device comprising a uterine placement handle at a proximate end of the uterine manipulator device and a tissue-penetrating component and a primary member of a device coupling mechanism at the distal end of the uterine manipulator device;
   perforating the uterine wall by utilization of the tissue-penetrating component of the uterine manipulator device;
   advancing the primary member of the device coupling mechanism of the uterine manipulator device through the perforated opening of the uterine wall;

advancing a distal end of a laparoscopic control device into the abdomino-pelvic cavity of a patient towards the perforated opening of the uterine wall, the laparoscopic control device comprising a proximate end and a distal end, wherein the proximate end of the laparoscopic control device comprises a device control handle and the distal end of the laparoscopic control device comprises a secondary member of the device coupling mechanism; and mechanically engaging the secondary member of the device coupling mechanism of the laparoscopic control device with the primary member of the device coupling mechanism of the uterine manipulator device, resulting in the construction of an assembly comprising the laparoscopic control device and the uterine manipulator device, the assembly being under the control of the device control handle comprised at the proximate end of the laparoscopic control device, wherein the primary and secondary members of the device coupling mechanism comprise a latch-hook clasp closure apparatus, a bayonet closure apparatus, or a threaded closure apparatus.

5. The method of claim 4, further comprising physically stabilizing the uterine manipulator device within the vaginal and uterine cavities at a predetermined position.

6. The method of claim 5, wherein the laparoscopic uterine manipulator assembly is configured to allow an individual user to utilize the device control handle of the assembled device to control the assembled device in a manner that allows the user to engage and reposition the uterus.

7. The method of claim 6, further comprising the individual user utilizing a laparoscopic cutting instrument in conjunction with the laparoscopic uterine manipulator assembly to remove at least the uterus of the patient.

8. The method of claim 7, further comprising disassembling the laparoscopic uterine assembly by mechanically disengaging the laparoscopic control device from the uterine manipulator device.

9. The method of claim 8, further comprising withdrawing the uterine manipulator device from the vaginal cavity and the laparoscopic control device from the abdomino-pelvic cavity, and retrieving the severed uterus from the abdomino-pelvic cavity of the patient.

* * * * *